United States Patent
Abbott et al.

[11] Patent Number: 6,039,567
[45] Date of Patent: Mar. 21, 2000

[54] ARRANGEMENT FOR FEEDING ABRASIVE DENTAL POWDER

[75] Inventors: John D. Abbott, Redwood City; Arthur Vassiliadis, Dana Point, both of Calif.

[73] Assignee: Dove Systems, Inc., Redwood City, Calif.

[21] Appl. No.: 09/244,255

[22] Filed: Feb. 3, 1999

[51] Int. Cl.[7] ............................... A61C 3/02; B24C 7/00
[52] U.S. Cl. ............................................. 433/88; 451/99
[58] Field of Search .................. 433/80, 88, 89, 433/125, 216; 451/94, 99, 101

[56] References Cited

U.S. PATENT DOCUMENTS

| | | | |
|---|---|---|---|
| 1,664,369 | 3/1928 | Maurer | 433/88 |
| 3,074,822 | 1/1963 | Walk et al. | 451/94 |
| 3,411,213 | 11/1968 | Spinello | 433/89 |
| 4,707,951 | 11/1987 | Gibot et al. | 451/99 |
| 4,768,314 | 9/1988 | Thomson | 451/99 |
| 4,776,794 | 10/1988 | Meller | 433/216 |
| 4,970,830 | 11/1990 | Schlick | 451/99 |
| 5,099,619 | 3/1992 | Rose | 451/99 |
| 5,199,229 | 4/1993 | Herold et al. | 433/88 |
| 5,330,354 | 7/1994 | Gallant | 433/88 |
| 5,692,901 | 12/1997 | Roth et al. | 433/125 |
| 5,934,904 | 8/1999 | Elrod et al. | 433/88 |

FOREIGN PATENT DOCUMENTS

609491  10/1948  United Kingdom ............... 451/99

*Primary Examiner*—Ralph A. Lewis
*Attorney, Agent, or Firm*—Jeffrey Slusher

[57] ABSTRACT

A dental abrasion arrangement includes a pressure vessel that has an inlet port and an outlet port. A source of pressurized propellant gas is attached to the inlet port and a dental abrasion tool is attached to an outlet port of the pressure vessel. Abrasive powder is ejected from the pressure vessel and to the abrasion tool via a discharge assembly and the outlet port. A feeding and metering auger is mounted within the pressure vessel. The auger is mounted substantially horizontally within the pressure vessel. The auger is driven by a motor, so that the abrasive powder within the pressure vessel is fed to the discharge assembly as the motor causes the auger to rotate. The rotation of the auger, and thus the feed rate of powder to the tool, is preferably adjusted by a controller, which controls the rotation of the motor, preferably according to pre-determined profiles that take into account parameters such as the geometry of the auger and the dental tool, as well as variables such as the internal pressure in the pressure vessel. The outer casing of the pressure vessel can be made so small that it can be mounted on a standard dental tray, or on a supporting arm of a dental chair.

9 Claims, 10 Drawing Sheets

ARRANGEMENT FOR FEEDING ABRASIVE DENTAL POWDER

BACKGROUND OF THE INVENTION

1. Field of the Invention

This invention involves an arrangement for smooth and continuous feeding of pressurized abrasive material, in particular, for feeding abrasive powder in abrasive dental devices.

2. Description of the Related Art

A standing goal in dentistry is to find a way to efficiently and precisely reduce a tooth, for example, in preparation for a filling, or to remove plaque, with as little discomfort to the patient as possible. One promising alternative to the conventional rotating or vibrating mechanical drill bit is a tool that directs a fine stream of a pressurized abrasive powder against the surface of the tooth. Experience has indicated that these devices cause much less trauma to the tooth yet are at least as effective at removing tooth enamel as a conventional drill head. Moreover, since there is no hard physical contact between the surface of the tooth and a fast-vibrating or rotating drill bit or head, abrasive systems also reduce the risk of chipping the tooth surface.

The general technique of treating teeth using an abrasive jet is described in the following publications:

"Technic for Nonmechanical Preparation of Cavities and Prophylaxis," Robert Black, Journal of the American Dental Association, Vol. 32, pp. 955–965, 1945;

"Airbrasive: some fundamentals," Robert Black, Journal of the American Dental Association, Vol. 41, pp. 701–710, 1950;

"Airbrasive Technic Discussed," Harold Roach, Journal of the American Dental Association, Vol. 43, p. 108, 1951; and "Analysis of airbrasive procedures in dental practice," Sidney Epstein, Journal of the American Dental Association, Vol. 43, p. 578, 1951.

Known devices for treating teeth with an abrasive jet include those described in:

U.S. Pat. No. 2,696,049 (Black, Dec. 7, 1954);
U.S. Pat. No. 3,852,918 (Black, Dec. 10, 1974);
U.S. Pat. No. 4,412,402 (Gallant, Nov. 1, 1983);
U.S. Pat. No. 4,522,597 (Gallant, Jun. 11, 1985);
U.S. Pat. No. 4,635,897 (Gallant, Jan. 13, 1987);
U.S. Pat. No. 4,708,534 (Gallant, Nov. 24, 1987);
U.S. Pat. No. 4,733,503 (Gallant, Mar. 29, 1988);
U.S. Pat. No. 4,893,440 (Gallant et al., Jan. 16, 1990);
U.S. Pat. No. 5,275,561 (Goldsmith, Jan. 4, 1994);
U.S. Pat. No. 5,330,354 (Gallant, Jul. 19, 1994);
U.S. Pat. No. 5,334,016 (Goldsmith, Aug. 4, 1994);
U.S. Pat. No. 5,350,299 (Gallant, Sep. 27, 1994); and
International (PCT) Patent Application, Publication No. WO 93/10718 (Goldsmith, published Jun. 10, 1993).

Known devices such as these suffer from one or all of the following disadvantages:

1) their delivery rates are not precisely controlled, or even controllable, so that the rates vary greatly depending on how full their reservoirs are;

2) they are prone to clogging at least one point in the delivery path;

3) they do not efficiently use enough of the available pressure of the delivered propellant gas; and 4) they are too bulky or heavy to be easily mounted near the dentist, such as on the dental tray attached to the chair.

U.S. Pat. No. 5,618,177 (Abbott, Apr. 8, 1997) overcomes many problems of earlier systems in that it delivers a smooth flow of abrasive powder into the output gas stream. However, its inability to accurately meter, rather than just ensure, proper flow, as well as its size, means that an improved system is still needed. This invention provides such improvement.

One other shortcoming of existing arrangements for providing powder under pressure to an abrasive dental tool is that they require greater pressure to drive the powder than is generally available to other pneumatic dental tools such as a drill. It would be better for the abrasion tool to be able to use existing pressure sources, since this would eliminate the need to have multiple pressure sources or retrofitted manifolds.

SUMMARY OF THE INVENTION

The invention provides an arrangement for treating teeth with pressurized abrasive powder that includes a pressure vessel, which has, in turn, an inlet port, an outlet port, a discharge assembly, and a main pressure chamber holding a supply of abrasive powder. A source of pressurized gas is connected to the inlet port and a dental abrasion tool is connected to the outlet port. The abrasive powder is ejected from the pressure vessel and to the abrasion tool via the discharge assembly and the outlet port. A feeding and metering auger is also mounted within the pressure vessel. A motor is connected to the auger, and the abrasive powder within the pressure vessel is fed to the discharge assembly by motor-driven rotation of the auger.

In the preferred embodiment of the invention, a pressure transducer is included to sense the internal pressure in the pressure vessel. A controller is then also preferably connected to the motor for adjusting the rate of rotation of the motor, and thereby the feed rate of the auger, as a predetermined function of the internal pressure in the pressure vessel. The controller preferably includes a memory that stores pre-calibrated parameters of the pre-determined function of the internal pressure.

The auger may have any of several forms, depending on other design choices in the system. In the preferred embodiment, however, the auger has a coarse-feed auger portion and a fine-feed auger portion. The coarse-feed auger portion transports the abrasive powder substantially towards to the fine-feed auger portion and the fine-feed auger portion transports the powder toward and into the discharge assembly. The auger is preferably arranged substantially horizontally within the pressure vessel.

The arrangement according to the invention preferably also includes a sealing assembly for preventing leakage of the powder from the main pressure chamber to the motor. The auger preferably has a powder-clearing auger portion adjacent to the sealing assembly that moves powder within the main pressure chamber away from the motor.

Within the pressure vessel there is, furthermore, preferably a pressure inlet channel that connects the inlet port and the main pressure chamber; a powder ejection region in the discharge assembly; and a standpipe channel connecting the pressure inlet channel with the powder ejection region. A restriction member is preferably also located in the standpipe channel, the pressure in the ejection region thereby being held no lower than the pressure in the main pressure chamber during rotation of the auger.

In order to maintain the powder in a fluidized state before the powder enters the ejection region, the pressure vessel according to the invention preferably also has at least one blowpipe that opens, at one end, in the standpipe channel and that opens, at an opposite end, adjacent to the auger at the end of the auger nearest the discharge assembly. Pressurized gas is thereby directed through the blowpipe and onto the powder.

The preferred embodiment of the invention also includes a pinch valve assembly that has an open position, in which powder is free to pass from the pressure vessel and on to the dental abrasion tool via the outlet port, and a closed position, in which the powder is blocked from passing to the outlet port. The controller then also is provided for activating the pinch valve assembly in accordance with a user input signal to switch the pinch valve assembly between the open and closed positions.

The pressure vessel according to the invention can be made very small while still having greater efficiency than conventional systems for pressurizing abrasive powder in a propellant gas. The pressure vessel may, for example, have an outer casing no greater than 23 cm in length and no greater than 4.3 cm in width.

One advantage of the small size of the pressure vessel according to the invention is that its outer casing can be molded to conform to and be removably attached to a dental tray that is attached to a dental chair, or to a support arm that is attached to a dental chair.

BRIEF DESCRIPTION OF THE DRAWINGS

FIG. 1 illustrates one advantage of the invention, namely, that it is compact enough to be included in or on the dental chair itself.

DETAILED DESCRIPTION

Figure 1:
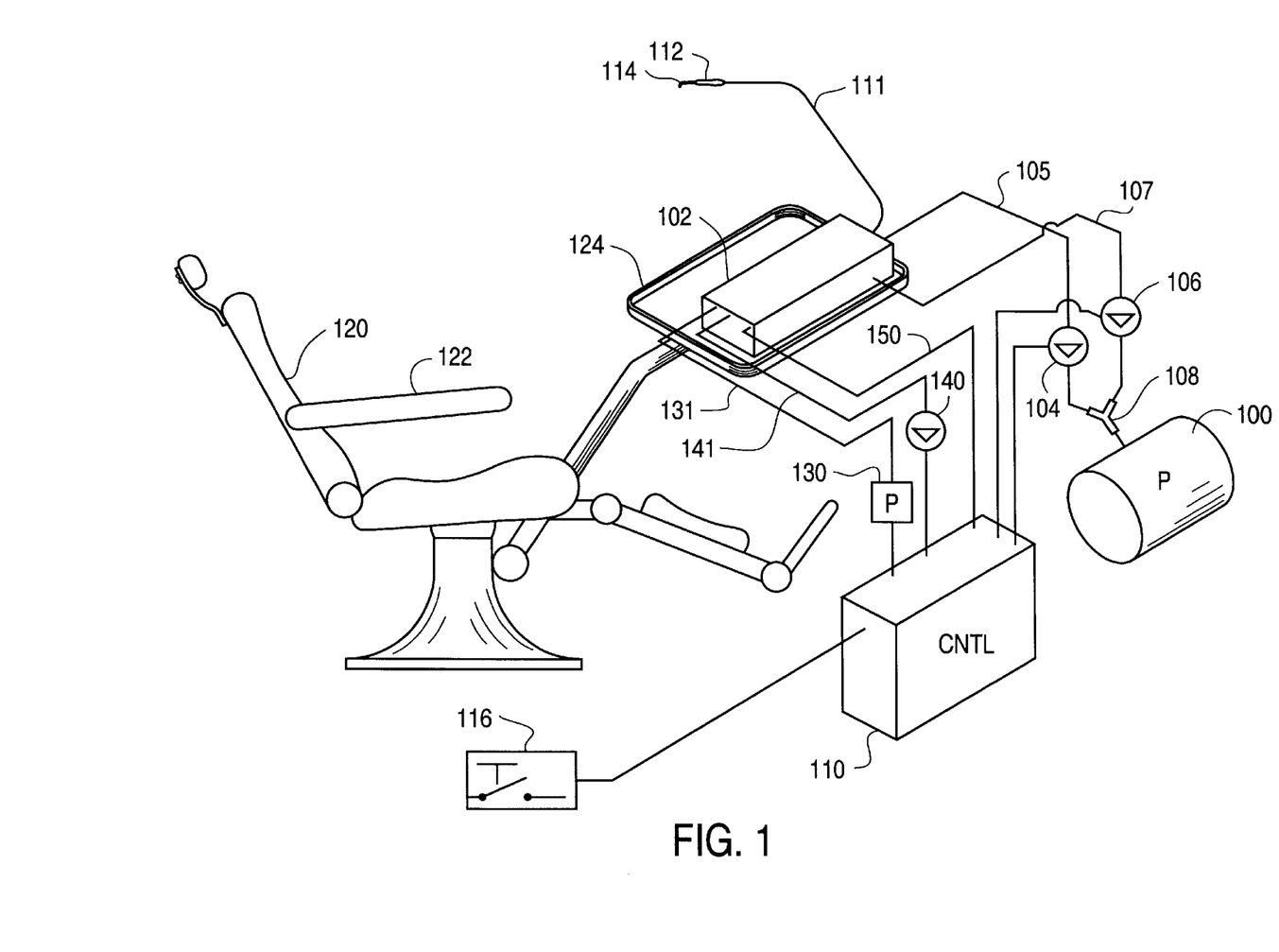
FIG. 1 not only illustrates the main components of the entire system according to the invention, but also shows the invention in use in a dentist's office. In particular.

FIG. 1 shows the main components of a system for treatment of teeth using an abrasive powder. These include a conventional pressure source 100, which delivers pressurized, propellant gas such as air or nitrogen. The propellant gas enters a fluidizing pressure vessel 102 by way of a normally closed valve 104 and a pressure inlet hose 105, that is connected via any conventional fitting to an inlet port 294 (see FIG. 2) of the pressure vessel.

Pressurized propellant gas is preferably also applied via a pinch valve inlet port 282 (see FIG. 5) to a pinch arrangement (described below) in the pressure vessel 102 (FIG. 1). A pinch valve hose 107 leads the gas via a valve 106 to the inlet port 282. The hose 107 may be connected to the inlet port 282 using any known fitting. The valve 106 is preferably normally open so that abrasive powder will be delivered only when demanded by the dentist. In FIG. 1, gas to the inlet and pinch valve is taken from a single outlet on the pressure source and distributed via, for example, a Y-connector 108 or a manifold block. The two valve/hose pairs 104, 105 and 106 may, however, of course be connected to a manifold block, to separate outlets of the pressure source 100, or built into the pressure vessel 102 so that only a single hose would be needed. A controller 110 is electrically connected to the valves 104 and 106 in order to control their state, that is, to open and close them independently, in a manner described below.

An outlet hose 111 is connected to an outlet port of the pressure vessel to carry abrasive powder, contained in the pressure vessel, under pressure to a hand-held abrasion tool 112. The tool 112 typically includes a metal nozzle 114 though which the abrasive material is propelled as a high-speed jet against the surface of a patient's tooth.

A foot switch 116 is preferably connected to the controller 110. When the dentist wants to activate the tool 112, that is, when he wants the pressure vessel to deliver abrasive powder under pressure to the tool 112, he may then step on the foot switch. This arrangement is well known, and is used to control even existing dental drills. The switch may, however, also be incorporated into the tool 114, or into any device where it will be convenient for the dentist to operate it.

The invention effectively delivers a wide range of particles under pressure. Any abrasive particles may be used according to the invention as long as they are fine enough to be fluidized and delivered in a propellant gas. Aluminum oxide is the generally preferred material for the abrasive treatment of teeth, and the invention is particularly advantageous for delivering this material, since it doesn't clog and has a very even delivery rate. The invention is not limited to use in the field of dentistry, however; it could, for example, be used for the precise and powerful delivery of other abrasive particles, for example, for other medical applications such as dermabrasion, for etching glass, and for general dispensing of powdered chemicals, not just abrasive powders. For the sake of simplicity only, the invention is described below in the context of delivering an abrasive material and all such materials and particles are referred to below as the abrasive "powder."

The preferred application of the invention is as a dental tool. Accordingly, FIG. 1 shows it in that context. One advantage of the invention is that the pressure vessel 102 is compact, light and quiet enough to be built into a dental chair 120 itself. For example, the pressure vessel 102 may be attached to or even form a section of one arm 122 of the chair. For ease of access, however, it is preferable to mount the pressure vessel onto a dental tray 124, which is typically mounted on the end of one arm of a dental chair. If the invention is used in this configuration, then the dentist will have quick and easy access to the pressure vessel not only to fill it with abrasive powder, but also to monitor its operation and adjust control parameters described below. No part of the operation of the invention requires the chair itself, however, so it may also be provided to the dentist as an independent, free-standing unit or only with, for example, a slot to hold the tool 112.

A conventional pressure transducer 130 is preferably included either inside the outer casing of the pressure vessel 102, or in a line 131 attached to a pressure port 260 (see FIG. 2) of the vessel 102. The output of the pressure transducer is connected to the controller 110.

In order to bleed pressurized gas out of the pressure vessel, for example, when the system is turned off, a vent valve 140 is attached to a vent port 265 (see FIG. 2) of the pressure vessel, for example via a vent hose 141. The vent valve 140 is preferably normally open so that the user will not need to remember to bleed the system before turning it off. The vent valve is connected to the controller 110, which controls the state of the valve as described below.

As is explained below, a metering and feeding motor 230 (see FIG. 2) is included within the pressure vessel 102. The controller is connected to this motor via conductors 150 (FIG. 1), over which electrical power and motor drive signals are carried to the motor.

Figure 2:
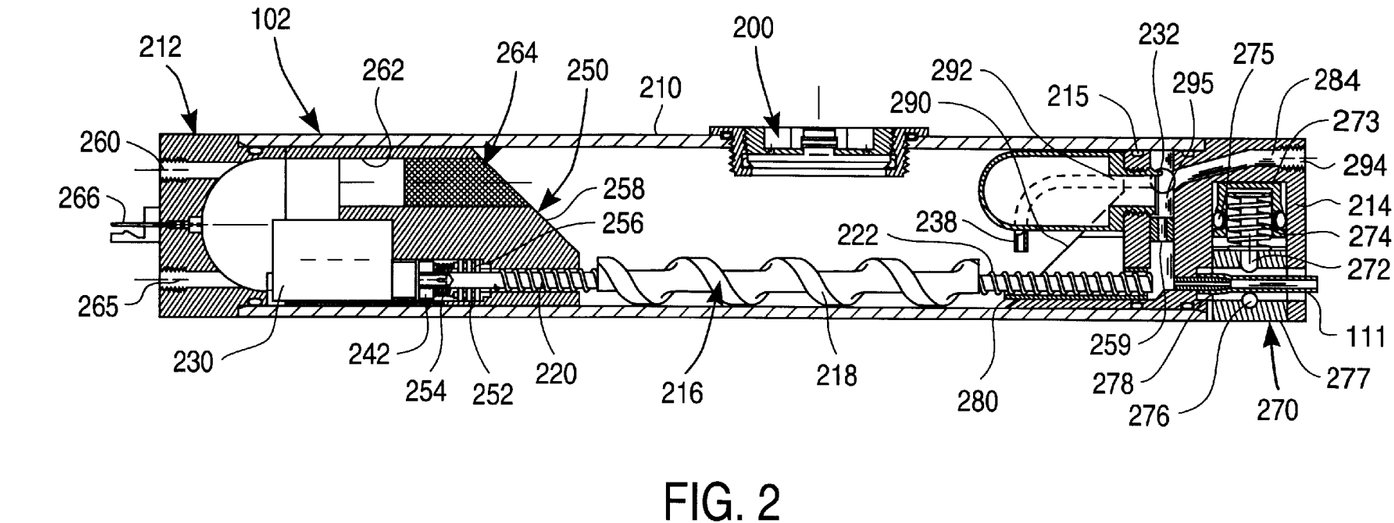
FIG. 2 is a cross-sectional side view of a preferred embodiment of the pressurization and feeding arrangement according to the invention.

FIG. 2 is a cross-sectional side view of a preferred embodiment of the pressure vessel 102 according to the invention. A removable powder filler cap 200 is shown screwed into a filler opening in the vessel 102. The cap 200 is sealed in any conventional manner, such as with O-rings or gaskets to ensure a tight seal when the interior of the pressure vessel is at operating pressure. In the preferred embodiment of the invention, the cap 200 is externally threaded and screws down into an internally threaded retaining member mounted in the outer wall of the pressure vessel. In order to fill the pressure vessel with abrasive powder, the user simply depressurizes the pressure vessel (described below), removes the cap 200, pours the powder into the pressure vessel, and then screws the cap securely back into place. The pressure vessel can then be re-pressurized.

Despite the small size of the pressure vessel according to the invention (see below), one filling with powder is usually sufficient to provide powder for many tooth reductions or other treatments. It is also possible, however, to feed powder into the pressure vessel 102 using a different, external arrangement, for example, a higher capacity hopper. The invention does not require any particular arrangement for filling the pressure vessel with abrasive powder.

The pressure vessel 102 includes a main outer wall 210 that is forms the housing for the system and is sealed at either end by end caps 212, 214. O-rings 215 or gaskets are preferably provided to seal the end caps 212, 214 against the main wall 210. The outer wall may have any convenient longitudinal cross-sectional shape (that is, viewed from one end to the other). It may be cylindrical or otherwise curved to conform, for example, to the dental tray or arm of the dental chair. The outer casing, or an optional, attachable mounting surface, may even be contoured to have a cross-sectional shape resembling an upside down "U" so as to fit easily yet securely over the arm of the dental tray.

In one working prototype of the invention, however, the outer wall had a mainly rectangular cross-section with dimensions 1.45 by 1.68 inches (roughly 3.68 by 4.27 cm). The total length of the pressure vessel, including end caps, was only 9 inches (about 23 cm). Even smaller prototypes work well, for example, with a longest side no greater than 1.25 inches (3.175 cm). The cross-sectional size will depend primarily on how much powder the pressure vessel is to hold at any one filling and the length will depend in part on how many components such as the pressure transducer and vent valve one chooses to include within the casing of the pressure vessel 102. The casing of the pressure vessel 102 may be made of any durable material, such as stainless steel or aluminum.

A metering feed auger or screw 216 is mounted mainly longitudinally and horizontally within the pressure chamber. In the preferred embodiment of the invention, the auger 216 has a relatively large-thread, large-diameter central portion 218 and relatively small-diameter portions 220, 222 on either side. The central auger portion 218 forms a coarse-feed auger and the portion 222 to its right (viewed as in FIG. 2) forms a fine-feed auger. As its name implies, one function of the feed auger 216 is to feed the powder that enters the pressure vessel toward a discharge arrangement, which is described below in detail. One additional function, especially of the small-diameter portion 220, is to prevent clogging of other mechanisms by powder; this is explained below.

The auger 216 may be machined from a single piece or assembled from separate pieces. The central portion 218 may, for example, be mounted like a sleeve over a shaft, with the smaller-diameter auger portions cut into the shaft at either end. In one prototype of the invention, a four-fluted, 3/8 inch (roughly, 0.953 cm) diameter ACME thread was used for the central portion 218 of the auger; this choice provided proper powder feeding with minimal clogging. The thread of the fine-feed auger portion 220 was chosen to be a simple, substantially straight buttressed thread. The auger portion 222 in one prototype was made as a 2-fluted 0.090 drill with 3/4 inch (1.9 cm) travel per turn and was used successfully in experiments with the invention. The threads of the end auger portions 220, 222 may be the same, as illustrated in FIG. 2. The threads for the various auger portions 218, 220, 222 may be different than those described here, however, and may be chosen using conventional experiments and normal design methods; indeed, in one early prototype of the invention, the coarse-feed auger portion 218 was formed simply by winding a wire around the auger shaft.

A motor 230 drives the auger 216 via a sealing, coupling arrangement. In one prototype of the invention, the shaft of the motor was connected to the auger 216 by means of a set screw collar 242. The motor and coupling arrangement are mounted in respective openings in a feed drive housing 250, which also helps not only to seal off the motor and coupling arrangement from the abrasive powder, but also to equalize pressure within the pressure chamber. To protect the motor from the pressurized powder in the interior of the pressure vessel, a seal 252 is preferably included around a smooth end portion of the auger and around a through-hole where the auger passes through the feed drive housing. To further ensure proper sealing by the seal 252, it preferably seats in a recess and is biased against the housing by a spring 254.

In a preferred embodiment of the invention, the seal 252 was formed as a series of rings mounted around the smooth end of the auger shaft. The rings were made of two materials: a first set of rings that were made of a relatively rigid and preferably abrasion-resistant polymer such as Delrin and a second set of rings made of a felt-like material such as chamois or felt itself. The rings were mounted alternatively, that is, Delrin-chamois-Delrin-chamois-Delrin. The Delrin rings were relatively thicker than the chamois (although this is not necessary) and were at both ends. Additional compression elements such as collars, made of any suitable, conventional material—including Delrin—may be mounted at either end or at both ends of this series of rings. In FIG. 2, one compression collar 256 is shown. The rings are slightly compressed by the spring 254, possibly via the end compression collars or outermost Delrin rings. Note that the outermost Delrin rings themselves may form the compression elements. The clearance between the Delrin rings and the inner surface of the bore in the housing 250 through which the auger shaft extends to the motor 230 was about 0.005 inches (about 0.127 mm) and the chamois rings actually contacted the inner surface.

It was discovered that this sealing ring arrangement provided excellent sealing, long life, and low friction. The rings of the felt-like material may also be lubricated using any lubricant that is approved for use within dental equipment. One other advantage of this sealing arrangement is that, the felt-like rings actually trap almost any abrasive powder that makes it past the rightmost (viewed as in FIG. 2) Delrin ring, without seizing and with no noticeable loss of performance. The number of rings used in the seal 252 may be chosen using normal design methods, taking into account the available space.

Other arrangements may, however, also be used instead of the alternating-ring seal described above. For example, one or more rubber O-rings may be used.

Note that it is not strictly necessary according to the invention to have the left-most, fine-feed auger portion 220. It is advantageous since it helps both move powder towards the coarse-feed auger portion 218 and help keep powder away from the motor and its coupling to the auger shaft. On the other hand, any other conventional arrangement may instead be included for sealing the motor against the abrasive powder and preventing loss of pressure past the motor. The portion, that is, shaft, of the auger to the left of the coarse-feed auger portion 218 may therefore even be smooth.

An innermost surface 258 of the feed drive housing 250 is preferably slanted so that powder that falls on it will tend to slide down toward the coarse feed auger portion 218. In a working prototype of the invention, its surface had a 45-degree downward slant, although this angle is not essential, but is easy to machine.

The pressure port 260 for the pressure transducer 131 (see FIG. 1) extends through the end cap 212 and, via a channel 262, into the main pressure chamber, that is, the region within the pressure vessel above the auger 216. A porous packing material 264 such as Porex or cotton is preferably provided in the channel 262 in order to act as a filter and prevent powder from passing through the channel 262 in case the pressure in the pressure chamber rises too far above that in the channel 262. As FIG. 2 shows, the inner surface of the packing material is preferably also slanted like the surface 258 to help ensure that powder falls down toward the auger.

It will occasionally be necessary to reduce or relieve all overpressure within the pressure vessel, for example, to relieve excess pressure or simply to relieve all overpressure within the vessel to allow the dentist to refill the vessel with powder. At these times, the controller 110 opens the vent valve 140, and the pressurized gas (such as air) within the pressure vessel then preferably vents to the outside through the filter 264, the channel 262, and out through the vent port 265.

The motor 230 is preferably controllable, so that the rotation of the auger 216 and thus the speed of feeding of the powder can be metered precisely. It is therefore preferable for the motor 230 to be a stepper motor of any conventional type. It would also be possible, however, to use a conventional continuous-drive DC motor as long as some arrangement were provided to monitor and control its rotational speed.

Electrical contacts 266 for the conductors (see FIG. 1) are provided to allow electrical power and control (such as stepping) signals to pass through the outer wall to the stepper motor. The point where the contacts pass through the end cap 212 is sealed using any known method to prevent pressure leaks from inside the pressure vessel.

To the right of the central auger portion 218 (viewed as in FIG. 2) is a pinch valve block assembly and a powder discharge arrangement according to the invention. The discharge assembly, as its name implies, is the assembly through which powder is ejected from the pressure vessel. The pinch valve block assembly 270 allows the system to stop powder and gas output even when the vessel is pressurized.

The pinch valve block assembly 270 includes a pin or valve stem 272 that is biased upward within a recess against a valve piston 273 by a spring 274. The periphery of the valve piston is preferably sealed against the inner wall of the recess by an O-ring 275. The valve stem 272 extends through a hole in an upper portion of a valve gate 277 and, in an extended position, into a longitudinal channel through the gate 277. Opposite the valve stem, in a lower portion of the valve gate 277, is a valve pinch member 276, which may be a simple metal pin that extends laterally (out of the plane of FIG. 2).

When pressurized gas is applied via the port 282, the valve piston 273 is forced downward, which also forces the valve stem 272 downward. This causes the outlet hose 111 to be pinched between the valve stem and the pinch member 276, thus cutting off the flow of powder and gas from the vessel. When the pressure to the port 282 is relieved, the spring 274 will force the valve piston and the valve stem back upward. The hose will then once again be open to permit the outward flow of gas and powder as long as there is pressure within the main pressure chamber of the vessel.

The outlet port for pressurized abrasive powder includes an outlet nozzle or jet 278, onto which the outlet hose 110 is slid. This arrangement is easy to maintain and provides adequate sealing, but the hose 110 may also be connected via some other conventional fitting. Since all abrasive powder will exit the unit under pressure through the outlet jet, the outlet jet is preferably made of metal such as carbide that can resist abrasion by the powder.

The outlet hose 110—at least that portion of it that connects to the outlet jet 278—is preferably made of vinyl tubing or of some other sturdy but elastic material. This is so that the hose can withstand abrasion yet still be flexible enough to slide over the jet and also be pinched off by the valve stem 272, which presses the hose against the member 276 when the stem is in its most extended position.

As with the feed drive housing 250, the pinch valve block assembly 270 has an innermost surface 290 that is preferably slanted so that powder that falls on it will tend to slide down toward either the fine feed auger portion 222 or the coarse feed auger portion 218; in a working prototype of the invention, the surface had a 45-degree downward slant, although this angle is not essential.

Pressurized propellant gas enters the main pressure chamber via the port 294, through a channel 284 that extends above (in the illustrated embodiment—other geometries are also permissible) the pinch valve block assembly 270, across a standpipe region 295, and through a packing arrangement that, similar to packing 264, acts as a filter 292 to prevent powder from exiting the main chamber except properly, that is, through the outlet port.

Figure 4:
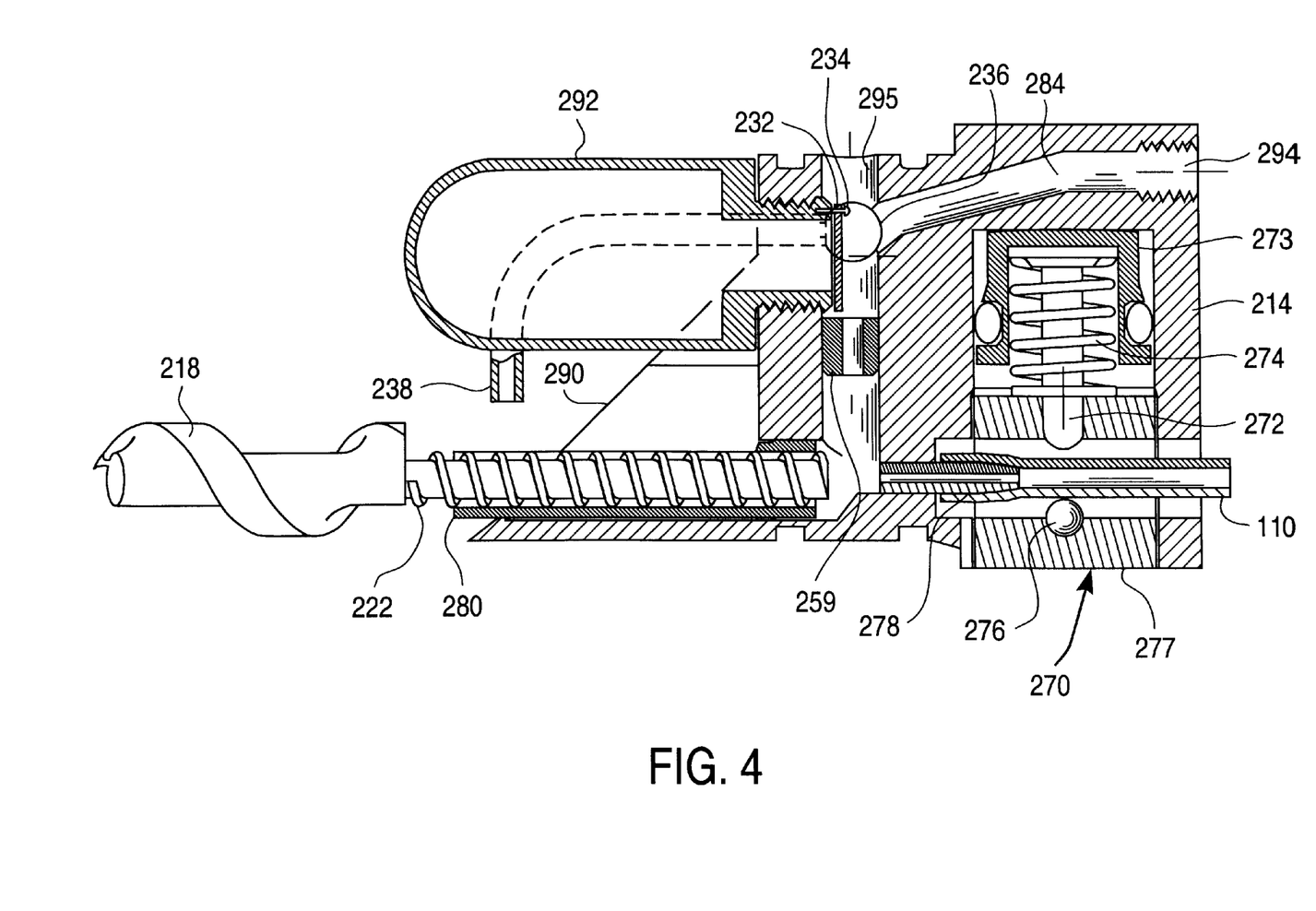
FIG. 4 is a partially exploded, cross-sectional view of a powder discharge arrangement and a pinch valve block assembly.

In the preferred, illustrated embodiment, the filter 292 is a Porex plug member that is inserted into an opening in the end cap/outlet assembly 214, for example, by simply press-fitting it into the opening, or by threading the member so that it can be screwed into a wall 286 of the outlet assembly; this is shown in FIG. 2, but is even clearer in FIG. 4. A simple filter packing made of cotton or some other porous filter material may be used instead of the Porex plug, but in most such cases the material will then need to be much thicker and will thus reduce the interior volume of the main pressure chamber. Furthermore, Porex has excellent filtering properties yet still allows high gas throughput.

A flapper valve 232 is preferably provided to cover the hole that otherwise allows air to pas through the filter member 292. The flapper valve 232 is described further in the discussion of FIG. 4, which shows the valve more clearly.

The rightmost end (viewed as in FIG. 2) of the auger 216 extends into a bushing formed by a sleeve 280. The sleeve 280 is preferably made of a durable polymer such as polyurethane or vinyl tubing and is preferably partially slitted or open upward so that powder can fall down onto the auger portion 222.

The sleeve 280 and coupling 242, 252 preferably support the small-diameter end portions of the auger 216 so that the coarse-feed portion 218 just clears the inner wall of the pressure vessel; this reduces wear on both the auger and wall, without allowing powder to accumulate unnecessarily below the auger. The powder itself thus forms a bearing material for the auger portion 222 against the sleeve 280—the motion of the powder is slow enough that abrasion of the sleeve is minimal, especially since the powder's velocity at the layer immediately adjacent to the sleeve's inner surface is essentially zero.

A mainly vertical channel or standpipe 295 extends from the inlet channel 284 down to the region between the end of the fine-feed auger portion 222 and the end of the nozzle 278 opposite the outlet hose 110. Air will thus flow from the pressure inlet 294, through the inlet channel 284, down the standpipe 295 and out through the nozzle 278 while carrying with it powder that has been delivered to the end of the auger portion 222.

A pair of blowpipes 238 open at one end in the standpipe 295 (through suitable holes in the block 214) and, at the other end, are directed onto the fine-feed auger portion 222. Some of the pressurized air that enters the standpipe 295 will then be directed via the blowpipes 238 onto the auger to help keep the powder there fluidized, that is, to prevent the powder from clumping, with the auger moving little or no powder through the "bore" hole in the clumped powder. The blowpipes 238 are, however, optional. It is also not necessary for there to be two blowpipes; rather, a single blowpipe may suffice.

Experiments have shown that the air and powder flow are improved by including a restriction 259 in the standpipe 295. In one prototype of the invention, the standpipe had an inner diameter of 0.187 inches (4.750 mm). The restriction was made as a plug with a vertical hole through it; the diameter of this hole was 0.062 inches (about 1.575 mm). The size of the restriction 259 may be chosen using normal experimentation. It's inner diameter should preferably be just small enough that the pressure at the bottom of the standpipe 295 is either the same as the pressure in the interior, main pressure chamber, or just slightly higher (to offset the pressure rise caused by the operation of the auger and motion of the powder within the sleeve 280).

One effect has been found to be that the air flow velocity, and thus the exit velocity of the powder, is increased by this restriction. Note first that pressurized input air (or other gas) is normally applied to the pressure vessel as pulses, preferably under the automatic control of the controller 110. It has further been found that, with the restriction 259, an oscillatory effect is created between the pressure in the standpipe and the pressure in the main pressure chamber of the vessel, as these two regions strive naturally for pressure equalization. The advantage of this oscillation has been found to be a reduction in powder use by as much as 50%, with 20% faster cutting ability on standard glass or ceramic test objects.

Figure 3:
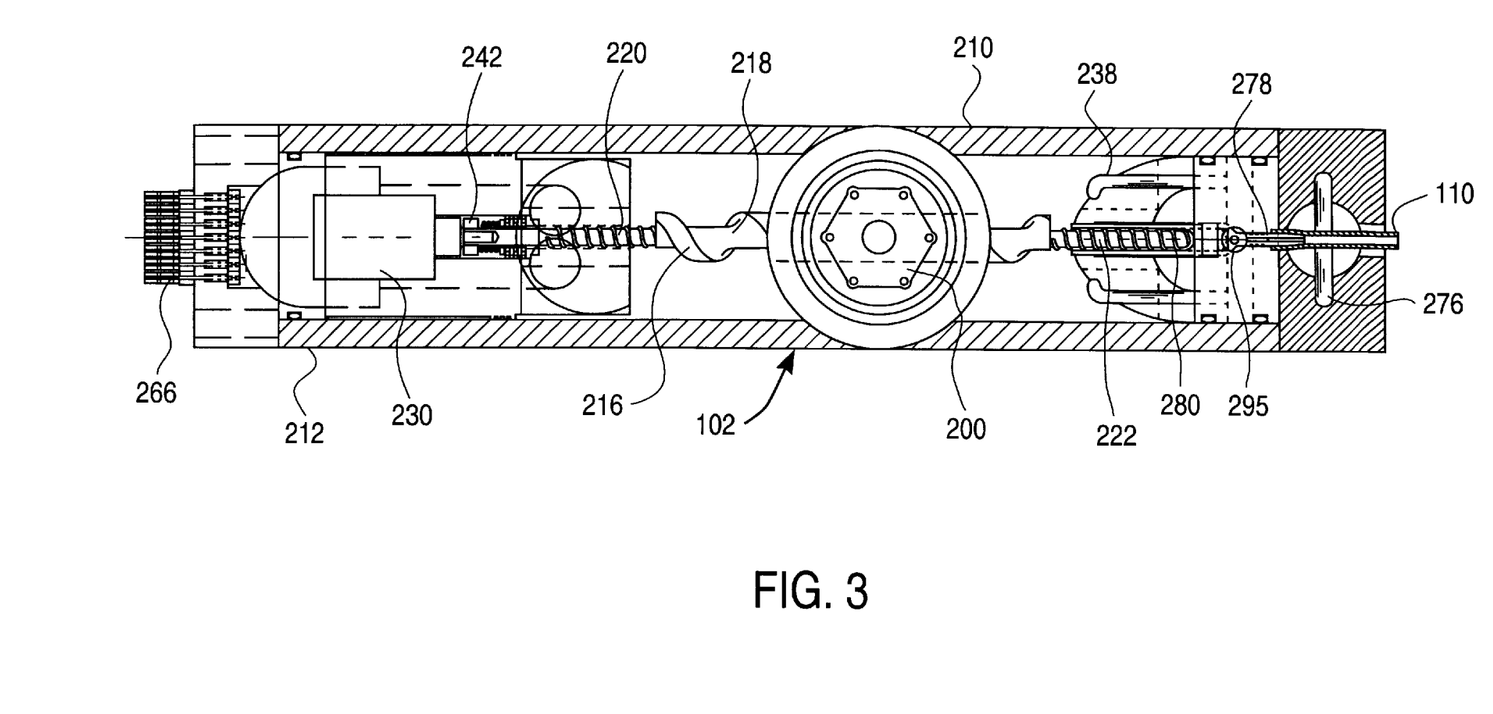
FIG. 3 is a cross-sectional top view of the arrangement shown in FIG. 2.

FIG. 3 is a partially cut-away view of the pressure vessel from the top. In this view, both blowpipes 238 are visible, and one can also see more clearly how the sleeve 280 is preferably upwardly open so that powder can fall down onto the fine-feed auger portion 222.

FIG. 4 is a partially exploded, cross-sectional view of the powder discharge arrangement and pinch valve block assembly 270 in the preferred embodiment of the invention. Note in particular the channel 284 that connects the input port 294 to the standpipe 295, and how the standpipe thereby connects the input port to the opening or bore through the outlet nozzle 278. Pressurized gas without powder thus reaches the nozzle 278 via the standpipe 295, whereas pressurized gas with powder reaches the nozzle from the main pressure chamber and past the auger portion 222 through the sleeve 280.

FIG. 4 also shows the flapper valve 232 is greater detail. The flapper may be made of any material such as plastic that is stiff enough to seal off the opening into the plug member 292 while still light enough to unseal the opening when there is back pressure through the plug member. For reasons of simplicity and ease of assembly, the flapper is preferably held in place by a pin 234; any other reliable pin or hinge arrangement may, however, be used. A transverse bore 236, which extends perpendicular to the plane of FIG. 4, is preferably provided to connect the intake ends of the two blowpipes 238 to ensure a flow of pressurized air to both.

The flapper valve 232 is both efficient and easy to implement. Any other conventional one-way valve arrangement, for example, a diaphragm, may, however, be used instead.

Figure 5:
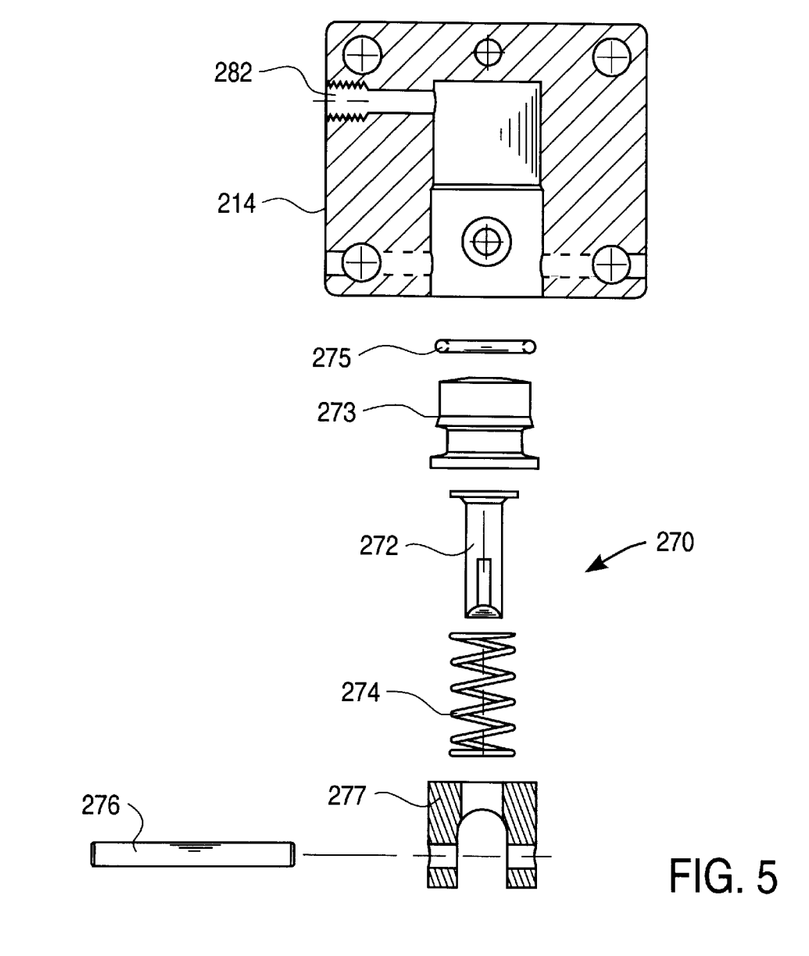
FIG. 5 is an exploded view of the pinch valve block assembly of FIG. 4.

FIG. 5 is an exploded view of the pinch valve block assembly 270. The view of FIG. 5 is from the right end of the assembly (viewed as in FIG. 2), in the plane of FIG. 2.

One of the several advantages of the invention is that only a single pinch valve is needed. Known arrangements need more than one because the powder is injected into these systems with such pressure that some arrangement must be included to allow purging of the outlet hose. Using this invention, it is possible to turn off the motor 230 (that is, stop active feeding of the powder) before the pinch valve is even closed. The outlet hose will still be purged, yet the powder purged from the hose may be used as part of the cutting operation. This is done by pre-programming the controller to take the residual pressure lag into account in calculating the feed rate of the system. This may be done through normal experimentation given the possible outlet hose diameters and lengths and the possible diameters of the orifice of the chosen tool tip 114. A 0.25 to 0.5 second lag time between motor stop and pinch valve closure has, for example, been adequate in tests of the invention to allow for proper purging. Note that this is not true "purging," but is rather clearing out bulk material in a useful way. Note also that the invention thus also reduces the possibility of clogging the outlet hose.

Figure 6:
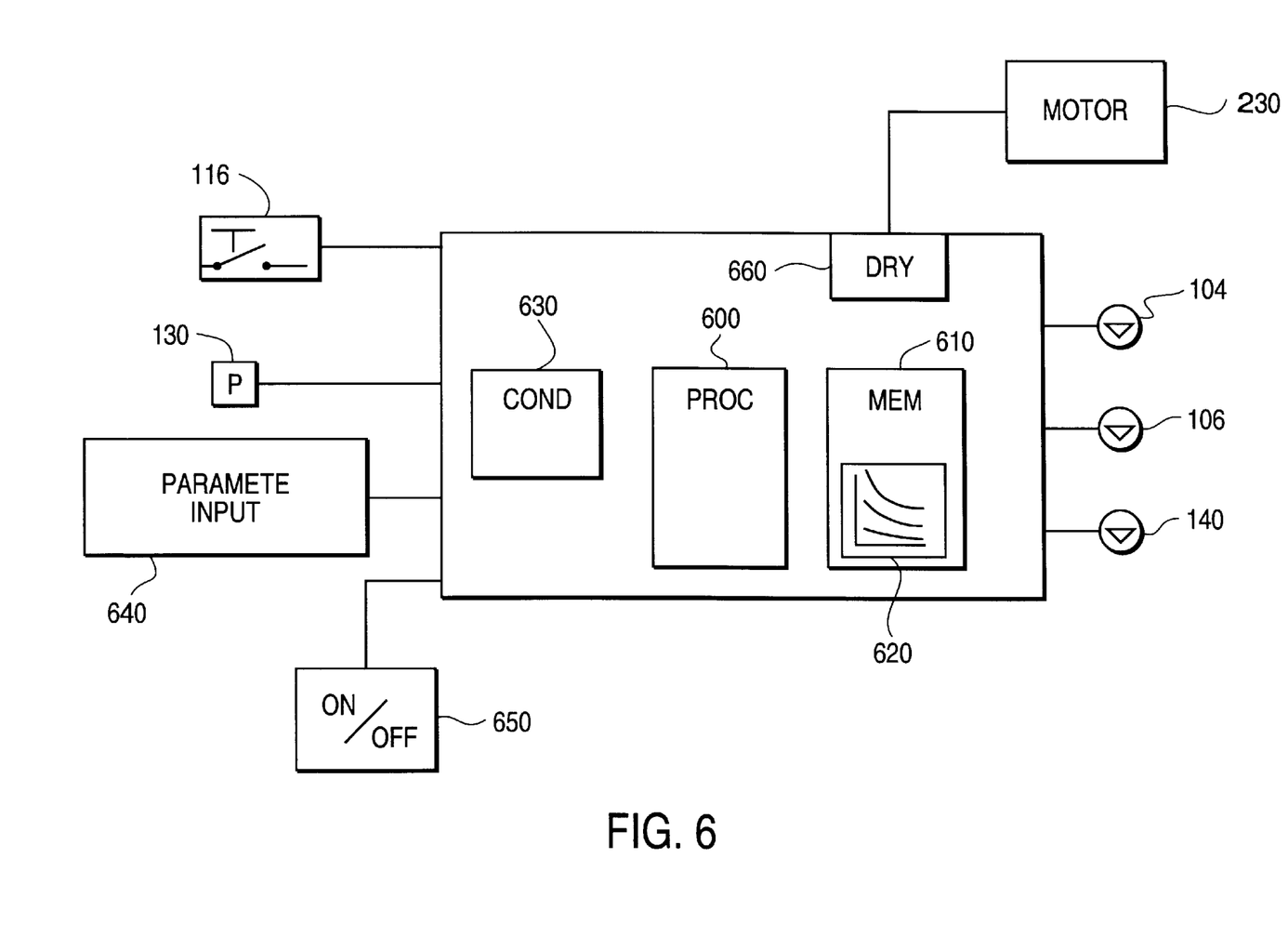
FIG. 6 is a block diagram of a controller.

FIG. 6 is a block diagram of the controller 110. The controller 110 includes a processor 600, which is preferably a programmable microprocessor in order to allow for maximum adaptability of the system to different types of abrasive dental tools that may be included in the total system. If the exact parameters of all tools, hoses and pressure sources is known in advance for all foreseeable possibilities, however, it would be possible use non-programmable circuitry to implement the processor 600.

A memory 610 is also included in the controller to store not only the operating instructions of the processor 600, but also a table 620 containing the operating parameters of the pressure vessel, motor, etc. This is explained further below. The memory will thus normally include static, non-volatile memory devices to store, for example, the processor's program, and RAM memory to store temporary values.

As is explained above, the foot (or other) switch 116 is connected to the controller 110 so that the controller will sense when the dentist needs pressurized, abrasive powder to be delivered to the tool 112 (FIG. 1). The pressure transducer 130 is similarly connected to the controller.

Conventional signal conditioning circuitry 630 is included in the controller 110. This conditioning circuitry may include, for example, an analog-to-digital converter to convert and, if needed, scale the analog pressure signal from the transducer 130 into the digital form needed for processing by the digital processor 600.

The necessary feed rate of the powder is a function of, among other parameters, the size of the orifice of the dental tool 112. During any given use of the invention, parameters such as these remain constant, but need to be available to the processor. A parameter input unit 640 is therefore preferably included in the invention. This unit may be as simple as a selector knob or a group of switches or buttons, but, for systems whose operating parameters might vary more often, it may also be a (preferably) small keypad. If no parameters are ever expected to change, however, the parameter input unit may be omitted, with the parameters being pre-stored in the memory 610.

An on/off switch 650 is preferably also included in the system and connected to the controller. Its function should, one would hope, be obvious even to those not skilled in the art of dental abrasion systems.

One of the main functions of the controller 110 is to control the rotational speed of the motor 230. Consequently, a motor drive circuit 660 is included in the controller. In the preferred case in which the motor is a stepper motor, the driver circuit will be the associated stepper driver. For DC motors, the drive circuit 660 will be a calibrated current or voltage source and will preferably include a digital-to-analog converter to convert the drive signals from the processor into a form suitable for use in driving the motor. The important feature is that the drive signals should cause the motor to rotate at a rate known either exactly (for a stepper motor), or at least with sufficient accuracy (for a non-stepper motor).

Normal experimental methods may be used to determine how fast the motor should turn in order to deliver a desired amount of powder for output from the pressure vessel to the tool 112. The parameters and variables will include at least the instantaneous pressure in the vessel (which is given by the pressure transducer), the size of the orifice of the tool 112, and the geometry of the coarse- and fine-feed auger portions 218, 222, but may also include the pressure decay rate when the tool is "purged" as described above, and the desired frequency at which pressure is applied to the pressure vessel via the inlet port. The relationship between, on the one hand, these variables and parameters, and, on the other hand, the output rate of abrasive powder, will be substantially constant, but, because it depends greatly on the particular choices of parameters made for any given implementation of the invention, it must be determined mainly through experiment. The feed rate of powder will, for example, depend not only on the geometry of the coarse- and fine-feed auger portions 218, 222, but also on the motor r.p.m., that is, on the rate of rotation of the auger. The relationship may therefore be determined and programmed into the controller simply by testing the system over the range of operating conditions expected, compiling the data in any conventional manner, and then storing the parametrized relationship as the table 620 in the memory 610.

FIGS. 7–10 illustrate test results comparing the improvement in performance of the invention as compared with one commercially available prior art device. For these tests, the prior art system was a commercially available implementation of the system disclosed in U.S. Pat. No. 5,618,177 (Abbott, Apr. 8, 1997). Substantially identical hand pieces (tools 112) were used on both systems in each comparative test.

Figure 7:
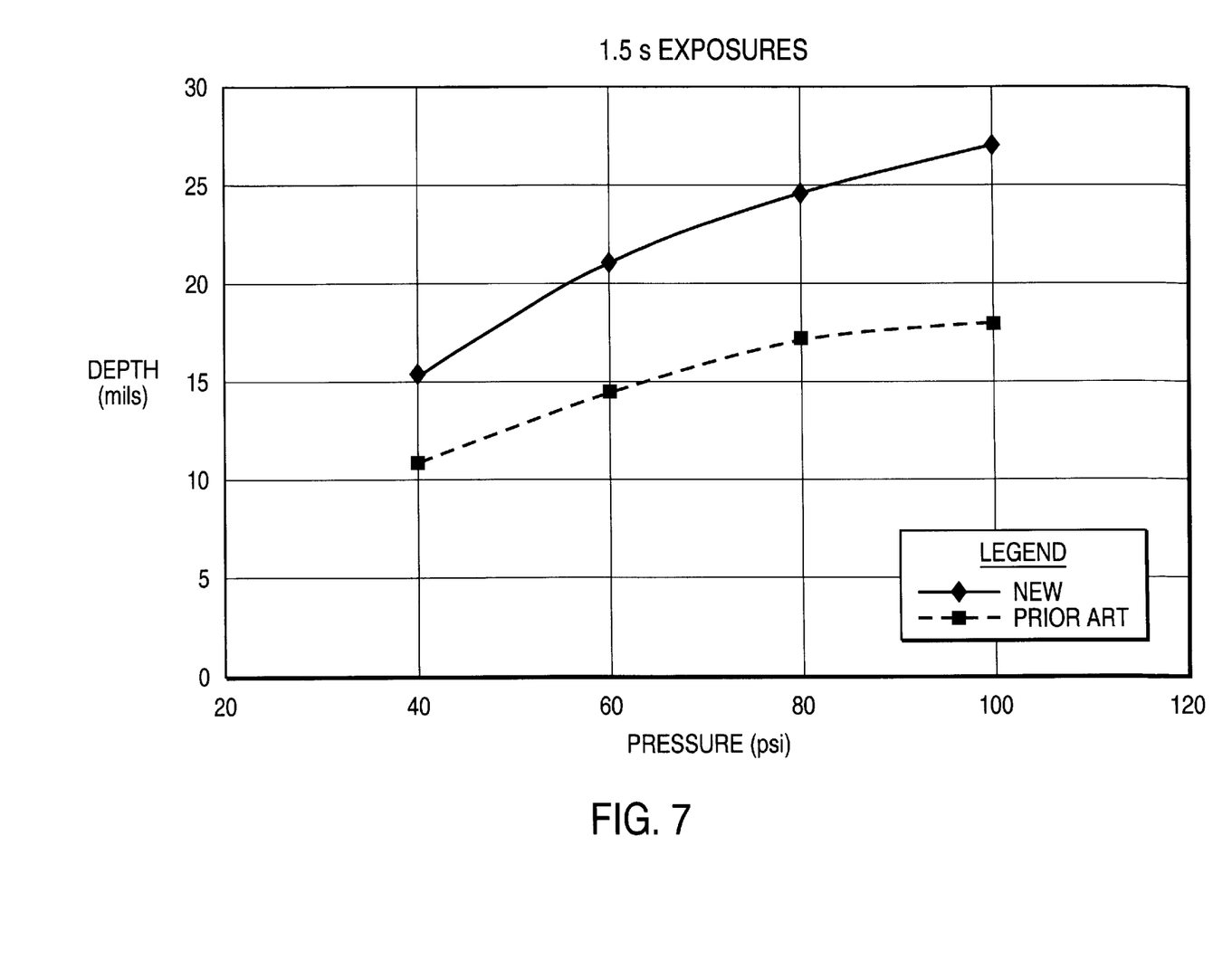
FIGS. 7–10 illustrate test results comparing the improvement in performance of the invention as compared with one commercially available prior art device.

FIG. 7 shows the depth of cut in mils of the respective systems as a function of vessel pressure in pounds per square inch (psi). The measurements were made by directing 1.5-second pulses of 50-micron abrasive aluminum oxide powder from the handpiece onto a standard microscope slide from a height 2 mm. Note that the invention performed much better (by more than 40%) than the prior art system over the entire pressure range.

Figure 8:
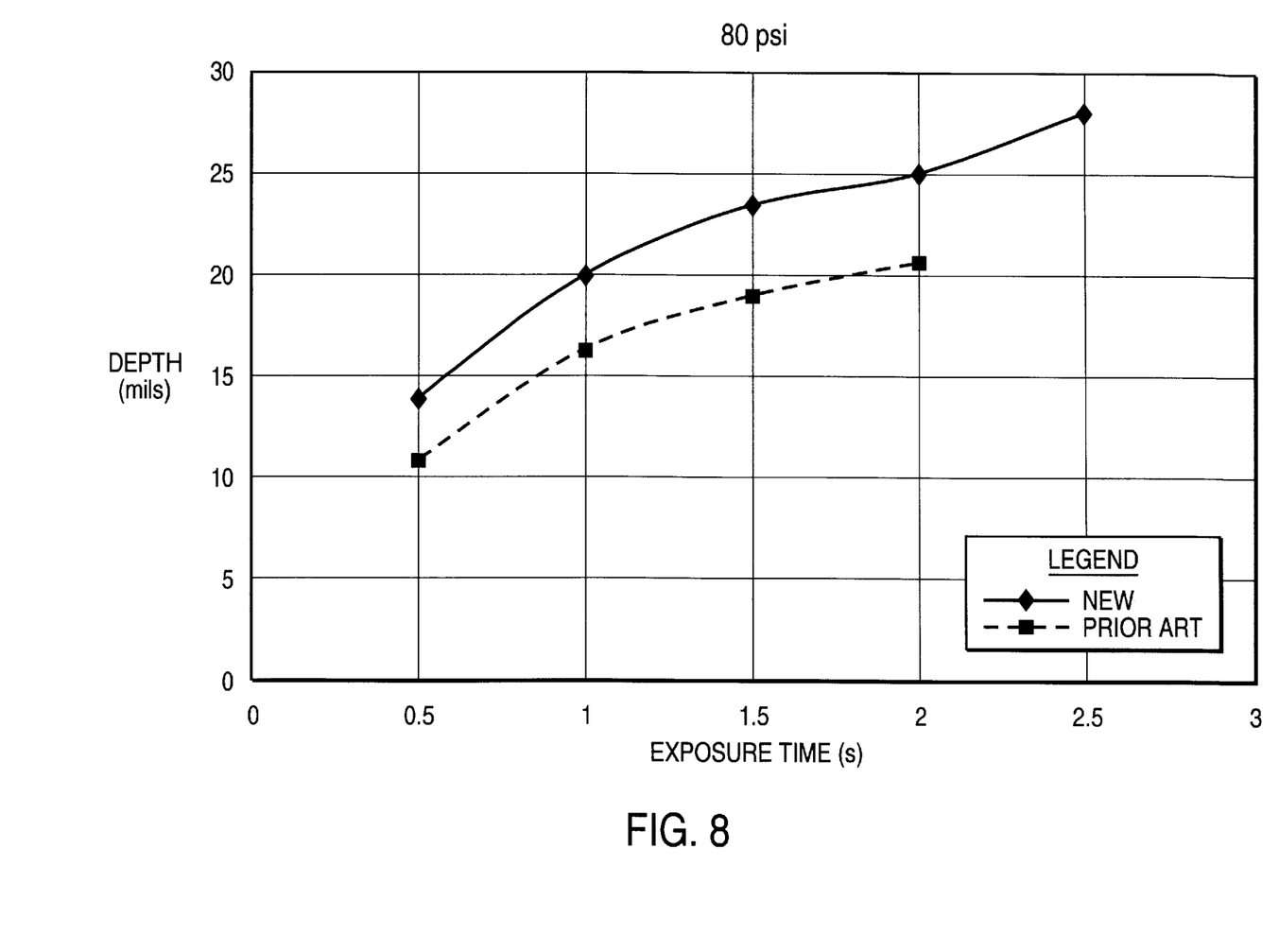

FIG. 8 shows the depth of cut in mils of the respective systems as a function of exposure time in seconds at a vessel pressure of 80 psi. As before, 50-micron powder was directed a standard microscope slide from a height of 2 mm. Again, note that the invention performed better than the prior art system for all exposure times.

Figure 9:
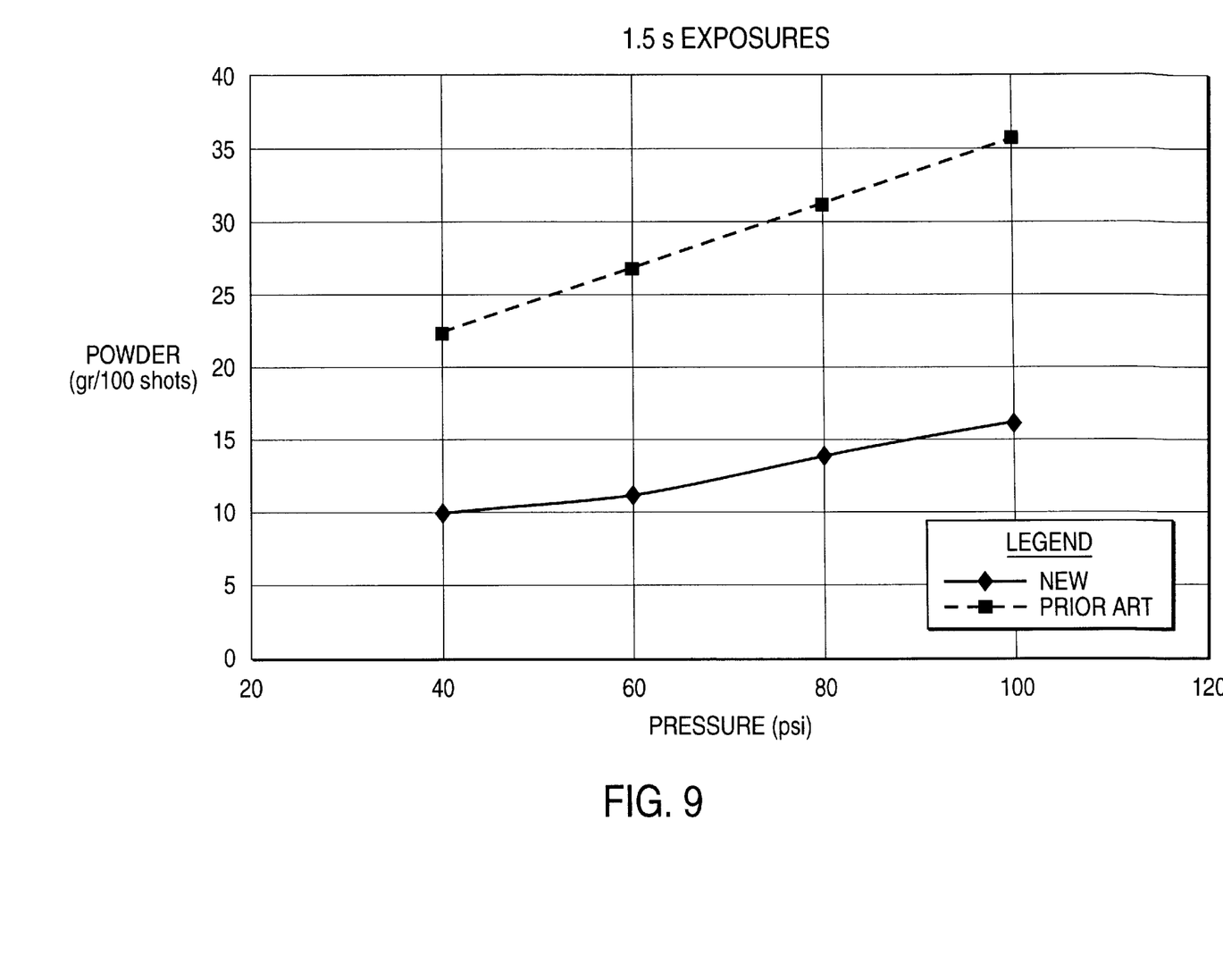

FIG. 9 shows the amount of powder (in grams) used by the respective systems for one-hundred 1.5-second exposures as a function of delivery pressure. Notice that the invention used far less powder than the prior art system, even though it cut deeper holes.

Figure 10:
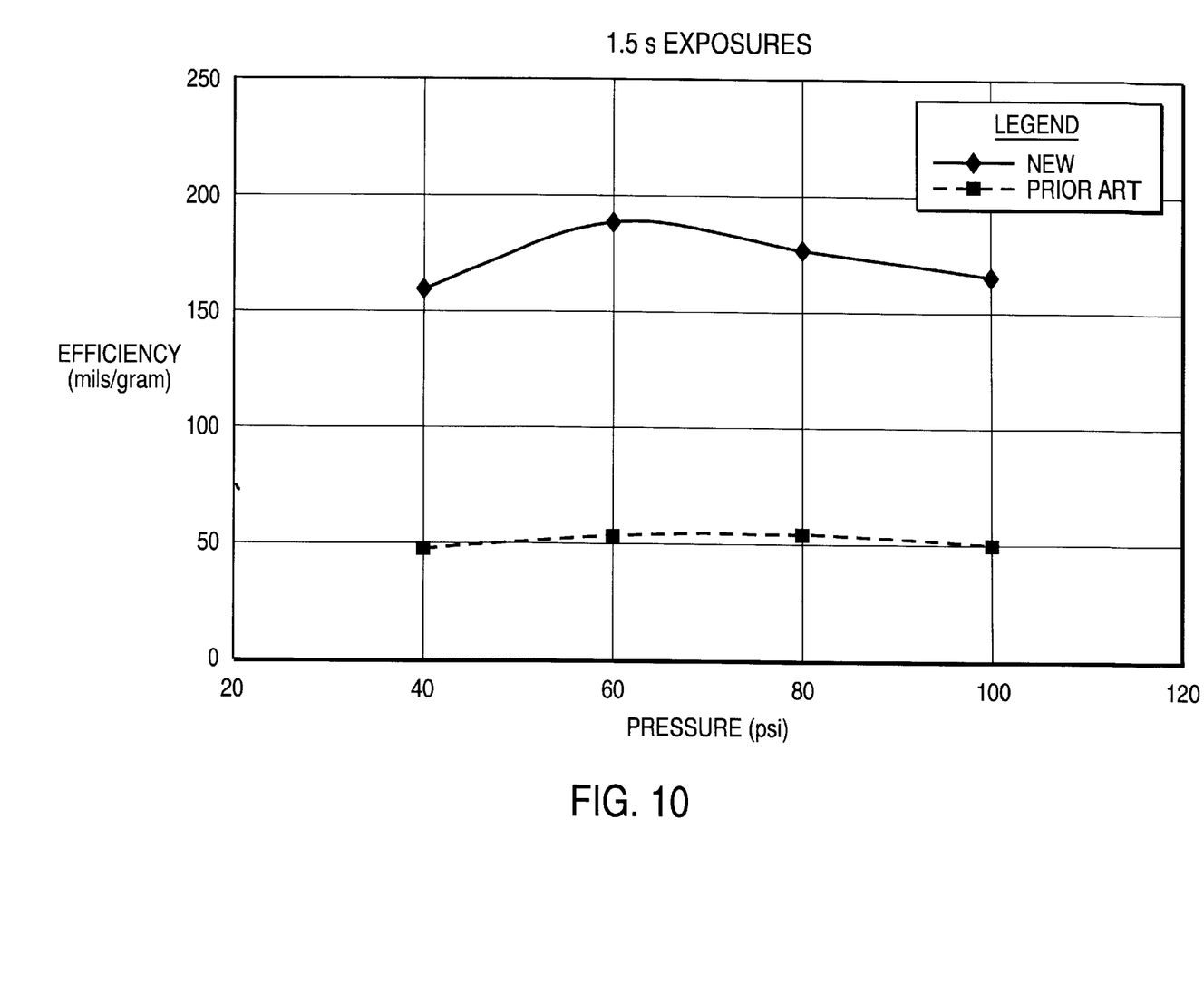

FIG. 10 shows the cutting efficiency of each system, calculated and plotted as a function of delivery pressure. Here, cutting efficiency is defined as the depth of the cut in mils divided by the amount of powder used in grams. As FIG. 10 illustrates, the efficiency of the invention was more than three times as great as the prior art system.

There are several reasons for the improved efficiency of the invention. One reason is, of course, the internal arrangement of the pressure vessel.

Another reason is that the auger used in the invention is both a feeding and a metering auger—its feed rate is preferably precisely controlled by driving the motor according both to pre-calculated, parameter-based profiles, and as a function of sensed instantaneous pressure in the pressure vessel. This is aided in part by the auger preferably being mounted substantially horizontally within the pressure vessel—no powder can simply "fall" out of the pressure vessel, but rather it must be fed, that is, metered, under precise control, to the outlet assembly. It is also possible, however, for the auger to be oriented vertically or at an angle, as long as the powder is properly fluidized and no "free flow" of powder is allowed, that is, as long as powder is ejected from the pressure vessel only when the motor is running and the auger is rotating.

In the preferred embodiment of the invention, the auger is a triple-function element: It provides a coarse, relatively high-volume powder movement toward the outlet; a fine, lower-volume powder movement into the outlet path; and a portion that helps prevent powder from compromising the integrity of the sealing arrangement between the auger and the motor. As is mentioned above, however, this third function—keeping powder away from the motor—may not be necessary (the auger portion 220 can be smooth) if the motor sealing arrangement is in itself sufficient to protect the motor during the expected life of the system. Even this simplified dual-function auger, however, retains the other advantages of having the coarse- and fine-feed auger portions.

Note that it is even possible to use an auger that has a uniform thread substantially over its entire length, thereby eliminating the distinction between the coarse-feed and fine-feed characteristic of the preferred auger illustrated in the figures and discussed above. In such cases it will be necessary to choose the threading and motor r.p.m. carefully, preferably after extensive experimentation, to ensure a steady and uniform flow of powder into the discharge assembly. Moreover, it may help ensure a proper supply of powder to the discharge assembly if the auger, or the entire pressure vessel, is mounted at an angle so that gravity will help move powder towards the outlet. As yet another alternative, a progressive thread could be used on the auger, such that, for example, the thread becomes progressively smaller from left to right (viewed as in FIG. 2). The auger could also be tapered, that is, at least approximately conical, with the wide end nearest the motor and the narrow end near the discharge assembly.

In certain cases, the dental device according to the invention can operate without any controller at all. For example, if the pressure into and within the pressure vessel is kept substantially constant by some other means, and if the geometry of the pressurized gas and powder paths (for example, in the hoses and through the dental tool 120) is known and fixed, then the motor could be driven at a constant rate. Alternatively, the motor rate could be adjusted manually, for example, by a potentiometer that the dentist can adjust by means of, for example, a knob mounted on the housing of the pressure vessel, or as an "accelerator pedal" in addition to the foot switch. The advantage of the controller 110, however, is that it allows the feed rate of the powder to be optimized, since the motor (and thus auger) rotation rate can be varied for any chosen operating pressure.

What is claimed is:

1. An arrangement for treating teeth with pressurized abrasive powder comprising:
    a pressure vessel with an inlet port, an outlet port, a discharge assembly, and a main pressure chamber holding a supply of abrasive powder;
    a source of pressurized gas connected to the inlet port;
    a dental abrasion tool connected to the outlet port, the abrasive powder being ejected from the pressure vessel and to the abrasion tool via the discharge assembly and the outlet port;
    a feeding and metering auger mounted within the pressure vessel;
    a motor that is connected to the auger, the abrasive powder within the pressure vessel being fed to the discharge assembly by motor-driven rotation of the auger;
    a pressure transducer sensing an internal pressure in the pressure vessel; and
    control means connected to the motor for adjusting a rate of rotation of the motor, and thereby a feed rate of the auger, as a pre-determined function of the internal pressure in the pressure vessel.

2. An arrangement as in claim 1, in which the control means includes a memory storing pre-calibrated parameters of the pre-determined function of the internal pressure.

3. An arrangement for treating teeth with pressurized abrasive powder comprising:
    a pressure vessel with an inlet port, an outlet port, a discharge assembly, and a main pressure chamber holding a supply of abrasive powder;
    a source of pressurized gas connected to the inlet port;
    a dental abrasion tool connected to the outlet port, the abrasive powder being ejected from the pressure vessel and to the abrasion tool via the discharge assembly and the outlet port;
    a feeding and metering auger mounted within the pressure vessel;
    a motor that is connected to the auger, the abrasive powder within the pressure vessel being fed to the discharge assembly by motor-driven rotation of the auger;
    a pressure transducer sensing an internal pressure in the pressure vessel;
    control means connected to the motor for adjusting a rate of rotation of the motor, and thereby a feed rate of the auger, as a pre-determined function of the internal pressure in the pressure vessel;
    a sealing assembly preventing leakage of the powder from the main pressure chamber to the motor;
    a powder clearing auger portion adjacent to the sealing assembly and moving powder within the main pressure chamber away from the motor;
    a pressure inlet channel connecting the inlet port and the main pressure chamber;
    a powder ejection region in the discharge assembly;
    a standpipe channel connecting the pressure inlet channel with the powder ejection region;
    a restriction member located in the standpipe channel, the pressure in the ejection region thereby being held no lower than the pressure in the main pressure chamber during rotation of the auger;
    a pinch valve assembly that has an open position, the powder being free to pass from the pressure vessel and on to the dental abrasion tool via the outlet port, and a closed position, the powder being blocked from passing to the outlet port;
    in which:
    the control means includes a memory storing pre-calibrated parameters of the pre-determined function of the internal pressure;
    the auger is arranged substantially horizontally within the pressure vessel and comprises a coarse-feed auger portion and a fine-feed auger portion, the coarse-feed auger portion transporting the abrasive powder substantially towards to the fine-feed auger portion and the fine-feed auger portion transporting the powder toward and into the discharge assembly; and
    the control means is provided for activating the pinch valve assembly in accordance with a user input signal to switch the pinch valve assembly between the open and closed positions.

4. An arrangement for treating teeth with pressurized abrasive powder comprising:
    a pressure vessel with an inlet port, an outlet port, a discharge assembly, and a main pressure chamber holding a supply of abrasive powder;
    a source of pressurized gas connected to the inlet port;
    a dental abrasion tool connected to the outlet port, the abrasive powder being ejected from the pressure vessel and to the abrasion tool via the discharge assembly and the outlet port;
    a feeding and metering auger mounted within the pressure vessel; and a motor that is connected to the auger, the abrasive powder within the pressure vessel being fed to the discharge assembly by motor-driven rotation of the auger;

in which the auger comprises a coarse-feed auger portion and a fine-feed auger portion, the coarse-feed auger portion transporting the abrasive powder substantially towards to the fine-feed auger portion and the fine-feed auger portion transporting the powder toward and into the discharge assembly.

5. An arrangement for treating teeth with pressurized abrasive powder comprising:

a pressure vessel with an inlet port, an outlet port, a discharge assembly, and a main pressure chamber holding a supply of abrasive powder;

a source of pressurized gas connected to the inlet port;

a dental abrasion tool connected to the outlet port, the abrasive powder being ejected from the pressure vessel and to the abrasion tool via the discharge assembly and the outlet port;

a feeding and metering auger mounted within the pressure vessel;

a motor that is connected to the auger, the abrasive powder within the pressure vessel being fed to the discharge assembly by motor-driven rotation of the auger;

a pressure inlet channel connecting the inlet port and the main pressure chamber;

a powder ejection region in the discharge assembly;

a standpipe channel connecting the pressure inlet channel with the powder ejection region; and a restriction member located in the standpipe channel, the pressure in the ejection region thereby being held no lower than the pressure in the main pressure chamber during rotation of the auger.

6. An arrangement for treating teeth with pressurized abrasive powder comprising:

a pressure vessel with an inlet port, an outlet port, a discharge assembly, and a main pressure chamber holding a supply of abrasive powder;

a source of pressurized gas connected to the inlet port;

a dental abrasion tool connected to the outlet port, the abrasive powder being ejected from the pressure vessel and to the abrasion tool via the discharge assembly and the outlet port;

a feeding and metering auger mounted within the pressure vessel;

a motor that is connected to the auger, the abrasive powder within the pressure vessel being fed to the discharge assembly by motor-driven rotation of the auger;

a pressure inlet channel connecting the inlet port and the main pressure chamber;

a powder ejection region in the discharge assembly;

a standpipe channel connecting the pressure inlet channel with the powder ejection region; and a blowpipe that opens, at one end, in the standpipe channel and that opens, at an opposite end, adjacent to the auger at the end of the auger nearest the discharge assembly, pressurized gas thereby being directed through the blowpipe and onto the powder, thereby maintaining the powder in a fluidized state before the powder enters the ejection region.

7. An arrangement for treating teeth with pressurized abrasive powder comprising:

a pressure vessel with an inlet port, an outlet port, a discharge assembly, and a main pressure chamber holding a supply of abrasive powder;

a source of pressurized gas connected to the inlet port;

a dental abrasion tool connected to the outlet port, the abrasive powder being ejected from the pressure vessel and to the abrasion tool via the discharge assembly and the outlet port;

a feeding and metering auger mounted within the pressure vessel;

a motor that is connected to the auger, the abrasive powder within the pressure vessel being fed to the discharge assembly by motor-driven rotation of the auger; and a pinch valve assembly that has an open position, in which powder is free to pass from the pressure vessel and on to the dental abrasion tool via the outlet port, and a closed position, in which the powder is blocked from passing to the outlet port;

the control means being provided for activating the pinch valve assembly in accordance with a user input signal to switch the pinch valve assembly between the open and closed positions.

8. An arrangement for treating teeth with pressurized abrasive powder comprising:

a pressure vessel with an inlet port, an outlet port, a discharge assembly, and a main pressure chamber holding a supply of abrasive powder;

a source of pressurized gas connected to the inlet port;

a dental abrasion tool connected to the outlet port, the abrasive powder being ejected from the pressure vessel and to the abrasion tool via the discharge assembly and the outlet port;

a feeding and metering auger mounted within the pressure vessel;

a motor that is connected to the auger, the abrasive powder within the pressure vessel being fed to the discharge assembly by motor-driven rotation of the auger;

in which:

the pressure vessel has an outer casing molded to conform to and be removably attached to a dental tray that is attached to a dental chair.

9. An arrangement for treating teeth with pressurized abrasive powder comprising:

a pressure vessel with an inlet port, an outlet port, a discharge assembly, and a main pressure chamber holding a supply of abrasive powder;

a source of pressurized gas connected to the inlet port;

a dental abrasion tool connected to the outlet port, the abrasive powder being ejected from the pressure vessel and to the abrasion tool via the discharge assembly and the outlet port;

a feeding and metering auger mounted within the pressure vessel;

a motor that is connected to the auger, the abrasive powder within the pressure vessel being fed to the discharge assembly by motor-driven rotation of the auger;

in which:

the pressure vessel has an outer casing molded to conform to and be removably attached to a support arm that is attached to a dental chair.

* * * * *